US00PP22146P2

(12) United States Plant Patent
Zerr

(10) Patent No.: US PP22,146 P2
(45) Date of Patent: Sep. 13, 2011

(54) POINSETTIA PLANT NAMED 'SYEP216'

(50) Latin Name: *Euphorbia pulcherrima*
Varietal Denomination: SYEP216

(75) Inventor: Katharina Zerr, Hillscheid (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/800,166

(22) Filed: May 10, 2010

(51) Int. Cl.
*A01H 5/00* (2006.01)

(52) U.S. Cl. ..... Plt./303

(58) Field of Classification Search ..... Plt./303
See application file for complete search history.

*Primary Examiner* — June Hwu
(74) *Attorney, Agent, or Firm* — S. Matthew Edwards

(57) ABSTRACT

A new Poinsettia plant named 'SYEP216' particularly distinguished by cultivar has brilliant red bracts with creamy white speckles, dark green foliage, bracts and leaves with pointed lobes, mid season flowering, and about medium sized, tight plant habit.

1 Drawing Sheet

Latin name of the genus and species of the plant claimed: *Euphorbia pulcherrima.*

Varietal denomination: 'SYEP216'.

BACKGROUND OF THE NEW PLANT

The present invention comprises a new Poinsettia plant, botanically known as *Euphorbia pulcherrima* and hereinafter referred to by the variety name 'SYEP216'.

'SYEP216' is a product of a planned breeding program. The new cultivar has brilliant red bracts with creamy white speckles, dark green foliage, bracts and leaves with pointed lobes, mid season flowering, and about medium sized, tight plant habit.

'SYEP216' originates from a naturally occurring whole plant mutation discovered in the parent variety 'Fisson Jinglet' (U.S. Plant Pat. No. 13,721). The mutation was discovered in the late fall of 2004, among a population of approximately 1000 single stemmed young plants of the parent variety in Hillscheid, Germany. Terminal tip cuttings of the new mutation selection were propagated and further trialed. A single plant section was again then selected in 2005 as SYEP216'. Terminal cuttings were then propagated and grown from this selection in the late fall of 2005 in Hillscheid, Germany.

Examinations continued thereafter on a larger scale, and have demonstrated that the combination of characteristics as herein disclosed for 'SYEP216' are firmly fixed and are retained through successive generations of asexual reproduction.

A Plant Breeder's Right for this cultivar has not been applied for. 'SYEP216' has not been made publicly available more than one year prior to the filing of this application. 'SYEP216' has not been observed under all possible environmental conditions. The phenotype may vary significantly with variations in environment such as temperature, light intensity and day length.

BRIEF DESCRIPTION OF THE DRAWING(S)

The accompanying photographic drawing shows typical flower and foliage characteristics of 'SYEP216' with colors being as true as possible with an illustration of this type. The photographic drawing taken in late November 2009 in Enkhuizen, Netherlands, shows the top view of an approximately 18 week old flowering plant of the new variety.

DETAILED BOTANICAL DESCRIPTION

The measurements were taken in Hillscheid, Germany in early January 2010 on 23 week old plants that were grown on benches in a greenhouse. Culture of these plants had started in late July 2009 with planting rooted cuttings in 14 cm pots and terminal pinching of the apices about 2 weeks later. The plants were grown under natural day light in the fall (no black cloth to initiate earlier flowering) and at the moderately warm temperature of 18° C. for the bench heating.

Color Chart used: Royal Horticultural Society Colour Chart (R.H.S.) 2001

BRIEF SUMMARY OF INVENTION

The following observations, measurements, and comparisons describe plants grown on benches in a greenhouse in Hillscheid, Germany. The following traits have been repeatedly observed and are determined to be basic characteristics of the new variety. The combination of these characteristics distinguishes this Poinsettia plant as a new and distinct variety.

DIFFERENCES BETWEEN THE NEW VARIETY 'SYEP216' AND SIMILAR VARIETIES

TABLE 1

| | 'SYEP216' | 'Fisson Jinglit' (U.S. Plant Pat. No. 13,721) |
|---|---|---|
| Bract coloring response: | One week earlier | One week later |
| General plant size: | Slightly smaller | Slightly larger |
| General speckle color: | Cream-white | Mostly cream-white, a few may be white and pink |

TABLE 2

| | 'SYEP216' | 'Primero Glitter' (Unpatented) |
|---|---|---|
| Warm temperature culture, brack color is: | Less bluish hue of red | More bluish hue |
| Lobe shape: | More distinctly pointed | Less distinctly pointed |

Plant:

*Form, growth and habit.*—Low shrub, freely branching, with relatively thin stems slanting upright.

*Plant height* (*without pot*).—19-20 cm.

*Plant width.*—27-30 cm.

*Number of branches.*—8-10.

*Number of inflorescences.*—7-8.

Roots:

*Number of days to initiate roots.*—*About* 18-21 days at about 24 degrees C.

*Number of days to produce a rooted cutting.*—24-26 days at 22-24 degrees C.

*Type.*—Fine, a little fleshy, free branching.

*Color.*—RHS 158D.

Stem:

*Color of stem.*—RHS 137C, with a slight infusion of anthocyanin may occur, the resulting color is about RHS 147B.

*Length of stem.*—Approximately 8-11 cm.

*Internode length.*—1.5-2.5 cm.

*Diameter.*—0.3-0.5 cm.

*Texture.*—Glabrous.

Foliage:

*Arrangement.*—Alternate.

*Quantity.*—5-7 leaves per branch.

*Aspect.*—Petioles are more or less horizontally directed, while the leaf blades are slanting downwards.

*Immature leaf color, upper surface.*—RHS 137C.

*Immature leaf color, lower surface.*—RHS 137D.

*Mature leaf color, upper surface.*—Near RHS 139A.

*Mature leaf color, lower surface.*—RHS 139B.

*Leaf length.*—9.0-10.5 cm.

*Leaf width.*—7.8-9.5 cm.

*Shape.*—Ovate to deltoid, with distinct pointed lobes.

*Base shape.*—Obtuse to acute.

*Apex shape.*—Acuminate.

*Margin.*—Entire.

*Texture, upper surface.*—Glabrous.

*Texture, lower surface.*—Mostly flat and smooth, apart from the protruding veins in a pinnate pattern, with very short and fine hairs along the veins and the margins.

*Color of veins, upper surface.*—RHS 146B, with slightly RHS 182A at the base.

*Color of veins, lower surface.*—Near RHS 182D.

*Petiole color, upper surface.*—A dull RHS 184A.

*Petiole color, lower surface.*—RHS 176A.

*Petiole length.*—4.0-6.0 cm.

*Diameter of petiole.*—0.2-0.3 cm.

*Texture upper and lower surfaces.*—Smooth, almost glabrous, very few fine hairs may occur.

Inflorescence:

*Type.*—Terminal cyme with surrounding whorl of colored bracts.

*Flowering, botanically* (*opening of the stamen, shedding of pollen*).—Early December.

*Start of flowering, commercially* (*sufficiently colored bracts*).—Late November.

*Flowering response time.*—About 8-9 weeks from equinox.

*Duration of flowering.*—Generally good keeping quality, duration depends much on light and environment, at minimum 4-8 weeks of 'shelf' life.

*Fragrance.*—Absent.

*Shape of inflorescence.*—Rosette-like arrangement, bracts often slanting downwards.

*Diameter of inflorescence.*—22-25 cm.

*Inflorescence, vertical diameter.*—3.5-5.0 cm.

*Number of completely colored bracts per inflorescence* (*sized over* 2 *cm*).—11-13.

*Single bract, shape.*—Elliptical to deltoid, with strong, pointed lobes and a long, pointed tip.

*Bract, apex.*—Relatively long, acuminate.

*Bract, base.*—Acute or obtuse.

*Single bract, length* (*without petiole*).—10.5-12.5 cm, younger bracts diminishing in size.

*Single bract, width.*—7.8-9.5 cm.

*Bract main color, upper side.*—RHS 45A or 46B.

*Bract variegation color.*—RHS 155B, occasionally in places where the red of the bract underside is shining through, spots may appear partly pink, between RHS 55A and RHS55B.

*Bract color, lower side.*—Between RHS 46B and RHS 46C; RHS 155B appear, similar as on the upper side.

*Vein color, upper surface.*—RHS 46A, nearly indistinct.

*Vein color, lower surface.*—RHS 53D on the larger bracts with RHS 47A on the younger and smaller bracts.

*Texture, both surfaces.*—Flat or somewhat folded, with weak to moderate rugosity, glabrous.

*Bract petiole diameter.*—0.2-0.3 cm.

*Petiole color, upper surface.*—RHS 53A.

*Petiole color, lower surface.*—Variable, near RHS 47A or RHS 143C.

Cyme (true inflorescence):

*Cyme, diameter.*—1.5-2.5 cm.

*Number of cyathia.*—5-10, borne in a small cluster.

*Cyathium, shape.*—Ovate.

*Cyathium, diameter.*—0.4-0.5 cm.

*Cyathium, length.*—0.5-0.6 cm.

*Cyathium, color.*—RHS 143A, top is RHS 46C.

*Peduncle length.*—0.1-0.3 cm.

*Peduncle color.*—RHS 143C.

*Nectar cups.*—Usually one per cyathium.

*Nectur cup, width.*—Usually 0.4 cm.

*Nectar cup, color.*—Initially RHS 7A and matures closer to RHS 13A.

Reproductive organs:

*Stamen* (*actually reduced male florets*).—Usually in a bunch of 15-20 at the top of the cyathium.

*Shape.*—Strap-like.

*Filament length.*—0.3-0.4 cm.

*Filament color.*—RHS 46B.

*Anther color.*—RHS 11A.

*Anther diameter.*—0.1 cm.

*Pollen quantity.*—Moderate (normal quantity).

*Pollen color.*—RHS 12A.

*Pistil* (*female flower*).—One per cyathium, emerge from the top of the cyathium about 4-5 weeks after maturity of the stamen if light intensity is sufficient.

*Total length.*—About 1.0 cm.

*Stigma.*—Trifurcate, 6 lobed.

*Stigma color.*—Between RHS 46A and RHS 46B.

*Style, length.*—0.5-0.7 cm.

*Style color.*—RHS 46B, completely, or partly RHS 144D.

*Ovary shape.*—Ovate.

*Ovary length.*—0.4-0.5 cm.

*Ovary color.*—RHS 143A to RHS 143B.

*Fertility/seed set.*—No seed set observed, but appears fertile.

Disease/pest resistance: Disease/pest resistance has not been observed on this hybrid.

What is claimed is:

1. A new and distinct variety of Poinsettia plant named 'SYEP216' substantially as illustrated and described herein.

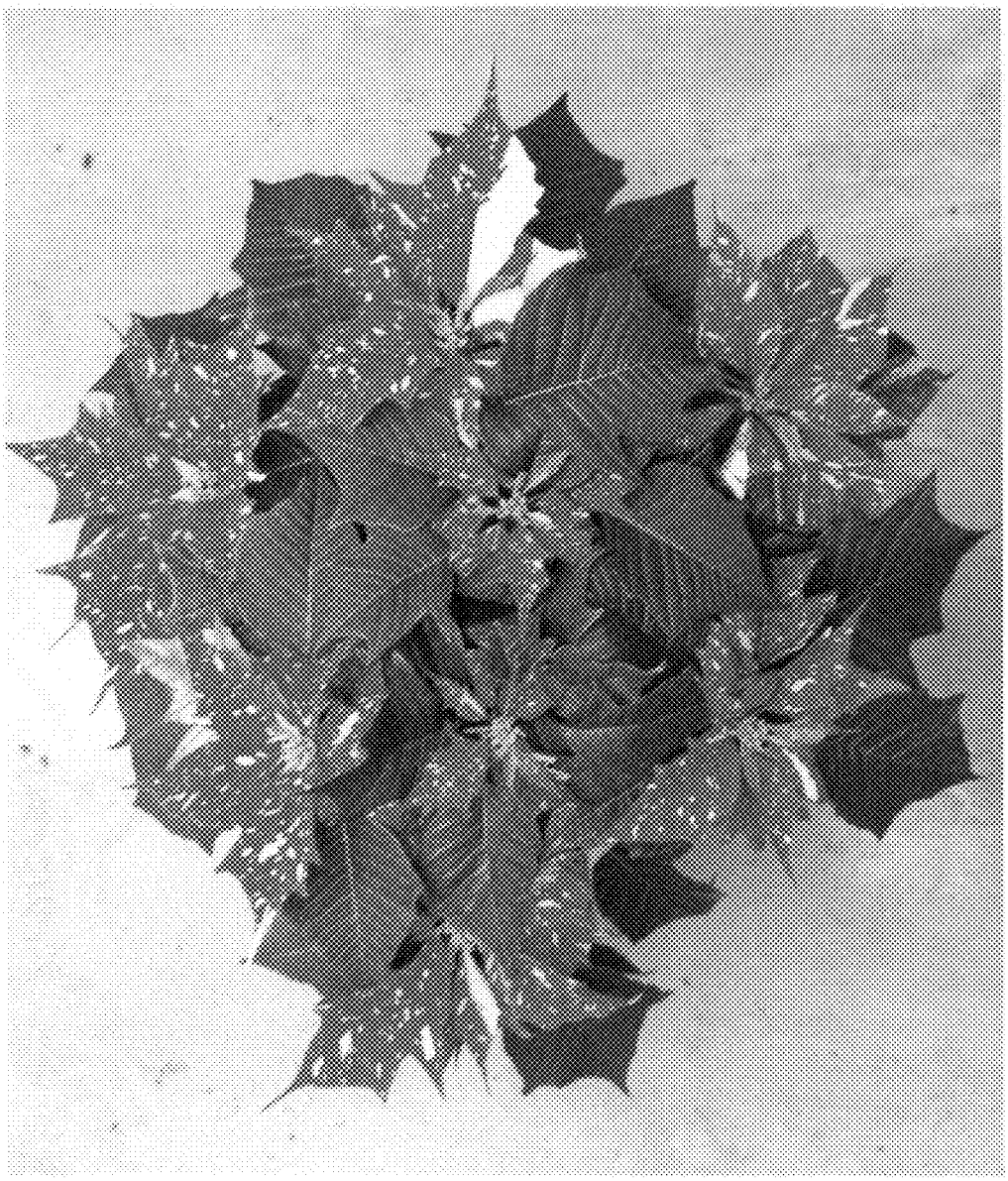

* * * * *